US005511558A

United States Patent [19]

Shepard et al.

[11] Patent Number: 5,511,558

[45] Date of Patent: Apr. 30, 1996

[54] BLOOD COLLECTION ASSEMBLY HAVING ADDITIVE DISPENSING MEANS AND METHOD FOR SAMPLE COLLECTION USING SAME

[75] Inventors: Thomas A. Shepard, Apex; Erwin A. Vogler, Newhill, both of N.C.

[73] Assignee: Becton, Dickinson and Company, Franklin Lakes, N.J.

[21] Appl. No.: 254,720

[22] Filed: Jun. 6, 1994

[51] Int. Cl.[6] .......... A61B 5/00

[52] U.S. Cl. .......... 128/760; 604/403; 604/415

[58] Field of Search .......... 128/760, 761, 128/762, 763, 764; 604/403, 408, 411, 415

[56] References Cited

U.S. PATENT DOCUMENTS

| | | | |
|---|---|---|---|
| 2,449,968 | 9/1948 | Smith | 604/415 X |
| 2,753,868 | 7/1956 | Seemar | 604/415 |
| 3,901,219 | 8/1975 | Kay | 128/764 |
| 4,159,229 | 5/1979 | Nugent | 128/764 |
| 4,396,613 | 8/1982 | Turner et al. | 128/760 X |
| 4,420,517 | 12/1983 | Ali . | |
| 4,580,577 | 4/1986 | O'Brien et al. | 128/760 |
| 4,675,159 | 6/1987 | Al-Siouffi | 128/764 X |
| 4,774,962 | 10/1988 | Hebel et al. | 128/760 |
| 5,065,768 | 11/1991 | Coleman et al. | 128/760 |
| 5,213,765 | 5/1993 | Kasai et al. . | |

FOREIGN PATENT DOCUMENTS

| | | | |
|---|---|---|---|
| 1155543 | 5/1958 | France | 604/415 |
| 3632303 | 4/1987 | Germany | 128/760 |
| 4119536 | 12/1992 | Germany | 604/415 |

*Primary Examiner*—Sam Rimell
*Attorney, Agent, or Firm*—Richard E. Brown

[57] ABSTRACT

A blood collection assembly includes an evacuated container having an open end with a puncturable stopper therein. A receptacle in the container contains an additive and has an open end covered by a puncturable, non-resealable material.

In a method for preparing a blood sample for analysis, the stopper and receptacle covering are punctured by a cannula, the cannula is partially retracted into the receptacle so that blood drawn through the cannula contacts the additive and washes it directly into the container through a hole in the covering made by the cannula.

5 Claims, 7 Drawing Sheets

BLOOD COLLECTION ASSEMBLY HAVING ADDITIVE DISPENSING MEANS AND METHOD FOR SAMPLE COLLECTION USING SAME

BACKGROUND OF THE INVENTION

1. Field of the Invention

This invention relates to blood collection, and, more particularly, relates to vacuum actuated tubes and a method for dispensing additives during blood draw.

2. Background

Blood samples are routinely taken in evacuated tubes. One end of a double-ended needle is inserted into a patient's vein. The other end of the needle then punctures a septum covering the open end of the tube so that the vacuum in the tube draws the blood sample through the needle into the tube. Using this technique, a plurality of samples can be taken using a single needle puncture of the skin.

Collection tubes are conventionally made of glass or plastic. Glass tubes have the advantage of liquid and gas impermeability. Plastic tubes are advantageous over glass in lower breakage, less weight in shipment and easier disposal by incineration, but high permeability to liquid and gas is a disadvantage. For example, polyethyleneterephthalate (PET), though widely used commercially for blood collection, has a limited shelf life due to water permeability.

Blood drawn into a tube is typically mixed with an additive present in the tube prior to draw. Clot activators such as silica particles promote rapid coagulation so that the liquid serum fraction can be readily separated from the clotted cells. Anticoagulants, such as citric acid, heparin or ethylenediaminetetraacetic acid (EDTA) are used to prevent clotting when the blood sample is to be used directly in hematological tests or to separate blood cells from the plasma.

The additive, whether procoagulant for clot activation or anticoagulant for clotting inhibition must be rapidly and thoroughly mixed with the blood sample to achieve its end use functionality. If the additive is present in the tube as a dry powder or salt, sound phlebotomist technique is critical to recognize when sufficient mixing cycles have been performed to completely dissolve or disperse the solid additive. Further, additives present in the tube in solution require precise concentrations to obtain reliable tube-to-tube performance. For such additives, water absorption or transmission through the tube must be eliminated to prevent inaccurate additive concentrations.

There is a need in the art of blood collection for a means of accurate storage and dispensing of tube additives that reduces dependence on phlebotomist technique and permits use of different plastics for tube manufacture. The present invention fulfills this need.

SUMMARY OF THE INVENTION

An assembly for collecting a blood sample includes a container, preferably evacuated, having an open end with a puncturable stopper therein. A receptacle having a side wall and a puncturable, non-resealable covering over an open bottom end has an additive for blood analysis therein. The preferred receptacle also has a puncturable covering over the top end and is positioned in the container below the stopper.

Another aspect of the invention is a method for preparing a blood sample for analysis using the assembly. The stopper and covering are punctured by a cannula connected to a blood supply, and the cannula is partially retracted into the receptacle leaving a hole in the covering resulting from the puncture. Blood is drawn into the receptacle by the pressure differential where it mixes with and carries the additive into the container.

Thus, the additive, whether in solid or liquid form, may be precisely measured and stored in a water impermeable receptacle which prevents any concentration changes even though a water permeable plastic is used for the container. Further, the additive is thoroughly mixed with the blood during draw and completely washed into the container in a procedure independent of phlebotomist technique.

DETAILED DESCRIPTION

Figure 1:
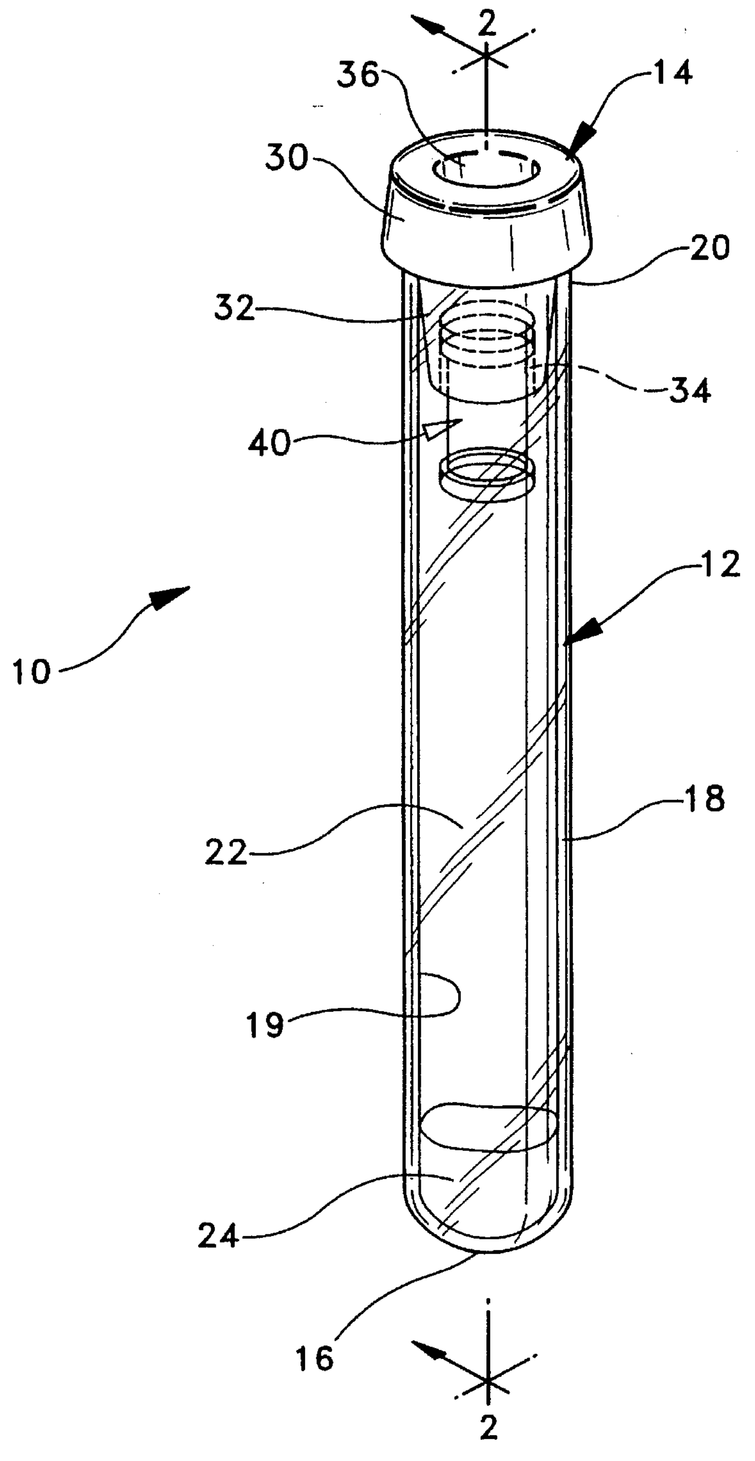
FIG. 1 is a perspective view of a blood collection assembly with a receptacle of the invention therein.

While this invention is satisfied by embodiments in many different forms, there will herein be described in detail preferred embodiments of the invention with the understanding that the present disclosure is to be considered as exemplary of the principles of the invention and is not intended to limit the invention to the embodiments illustrated and described. The scope of the invention will be measured by the appended claims and their equivalents.

The blood collection assembly of the invention may include any container having a closed end and an open end. Suitable containers are, for example bottles, vials, flasks and the like, preferably tubes. The container contains structure for storing an additive useful in preservation, separation or analysis of a blood sample taken in the container. The invention will henceforth be described in terms of the preferred tube.

Adverting now the drawings, FIGS. 1 to 5 illustrate a blood collection assembly 10 which includes a tube 12 and a puncturable stopper 14. Tube 12 has a bottom wall 16 and a side wall 18 having an inside wall surface 19. Sidewall 18 defines an open end 20 into which the stopper 14 may be placed. Bottom wall 16, side wall 18 and stopper 14 enclose an interior volume 22 of the tube which preferably contains a conventional serum separating gel 24 and preferably is evacuated. Evacuated tubes for blood collection are standard in the art.

Stopper 14 includes an annular upper portion 30 which extends over the top edge of the tube 12 and a lower annular portion or skirt 32 which extends into and forms an interference fit with inside wall surface 19 for maintaining stopper 14 in place in open end 20. Annular skirt 32 has a sidewall 33 which defines a well 34 and an annular upper portion 30 which defines a cavity 36. A septum portion 38 of annular upper portion 30 extends between well 34 and cavity 36 for puncture by a cannula (as described later).

Figure 3:
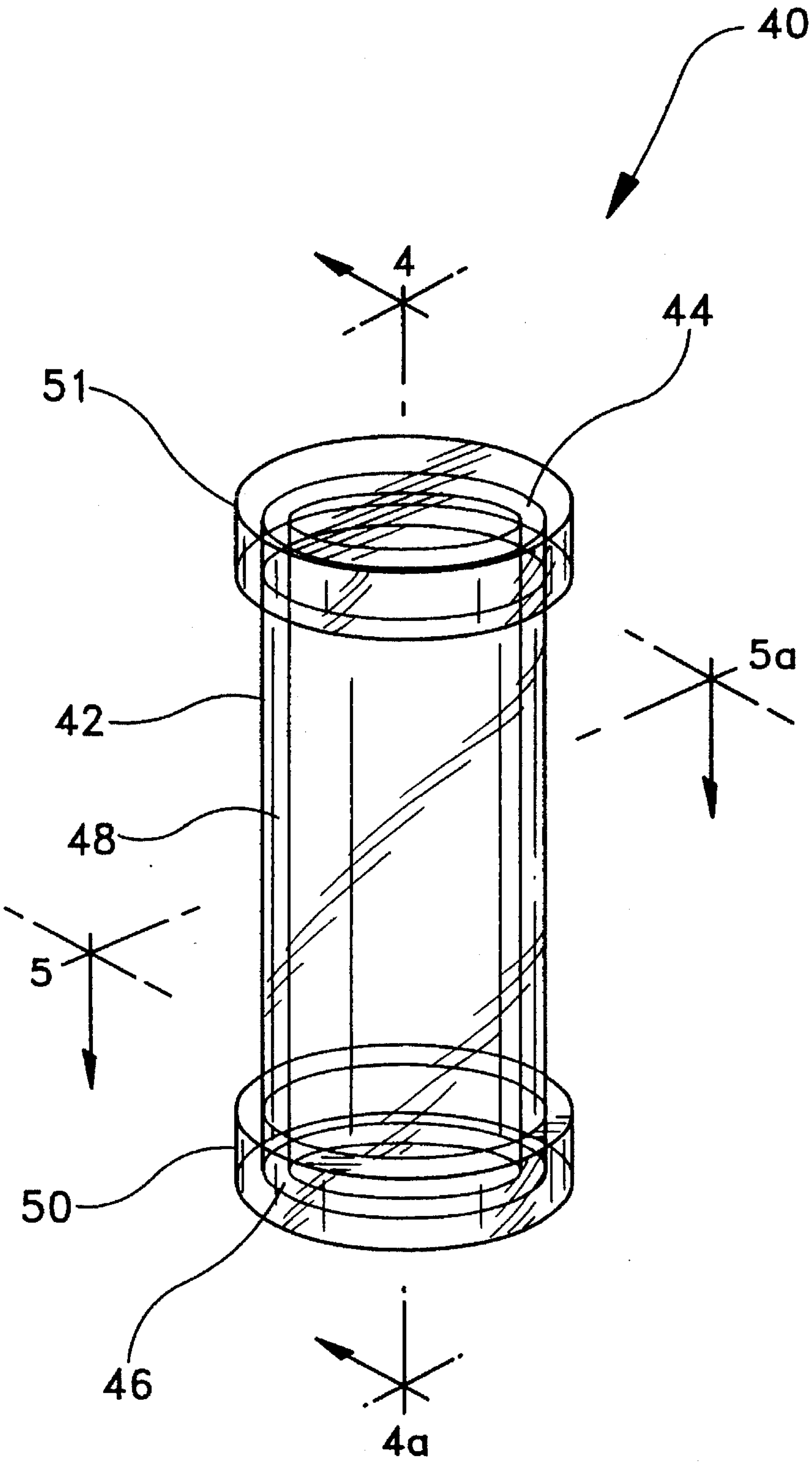
FIG. 3 is a perspective view of the receptacle of FIG. 1.
Figure 4:
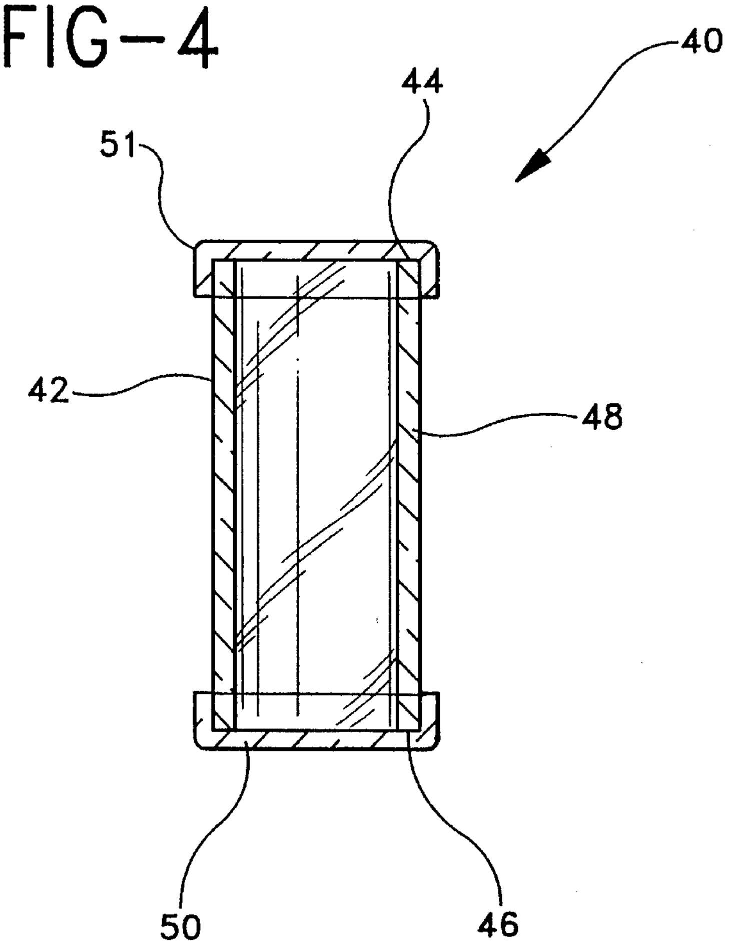
FIG. 4 is a vertical sectional view of the receptacle of FIG. 3 taken along the line 4–4_a_ thereof.
Figure 5:
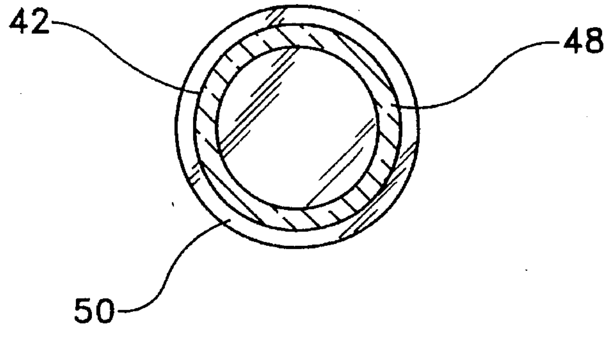
FIG. 5 is a horizontal sectional view of the receptacle of FIG. 3 taken along the line 5–5_a_ thereof.

A receptacle 40 for storage and delivery of an additive 41 for blood analysis may be immobilized in well 34. As shown in FIGS. 3–5, receptacle 40 may be a tube or barrel portion 42 having open top end 44, open bottom end 46, and side wall 48. Bottom end 46 has a puncturable, non-resealable covering 50 securely affixed to side wall 48. The preferred receptacle also optionally has a puncturable, non-resealable covering 51 over top end 44 securely affixed to side wall 48.

Receptacle 40 is sealably immobilized in well 34 by an interference fit between receptacle side wall 48 and side wall 33 of skirt 32. If receptacle 40 does not include covering 51, immobilization also includes a seal formed between the top of receptacle side wall 48 and septum portion 38 of annular upper portion 30 of stopper 14.

In the preferred assembly of the invention, tube 12 is evacuated and receptacle 40 is not evacuated.

Figure 6:
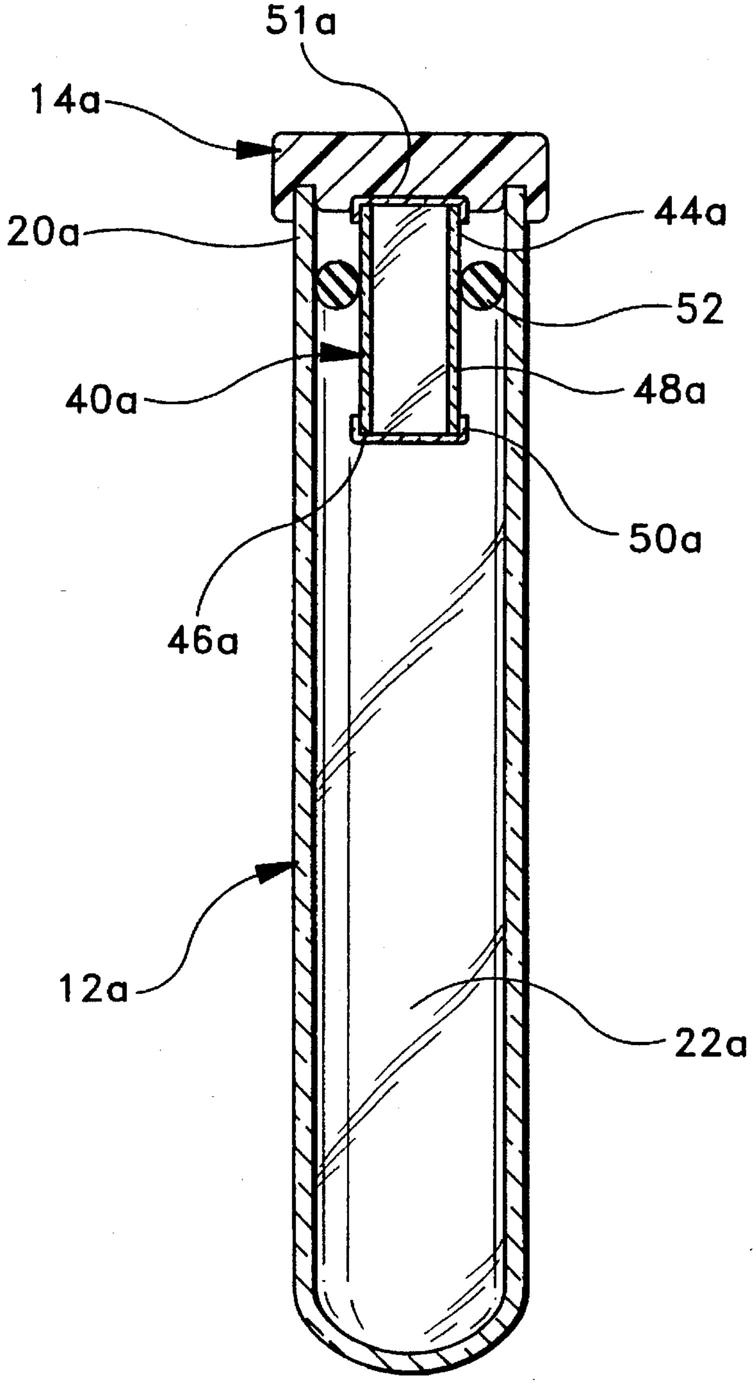
FIG. 6 illustrates an alternate embodiment of the assembly.

In another embodiment of the invention, the receptacle may be immobilized by any suitable means to the side wall of the tube, for example, by an interference fit between the tube and receptacle walls. Alternatively, as illustrated in FIG. 6 receptacle **40*a* is immobilized in tube interior volume 22*a* by, for example an elastomeric O-ring, 52. (In FIGS. 6–8**, elements similar to those previously described are given the same reference number followed by a letter suffix).

The tube my be of glass or preferably plastic. Suitable plastics are polypropylene (PP), polyethylene terephthalate (PET) and polystyrene (PS). While the tube may be of any size, the invention is particularly well suited to evacuated blood collection tubes. These tubes are generally cylindrical, 50 to 150 mm in length and about 10 to 20 mm in diameter. The stopper may be of any elastomer, as is well known in the art of evacuated blood collection tubes. Likewise the receptacle may be of plastic, such as PET or PS, but preferably is of a moisture and gas impermeable material such as plastic, metal, ceramic or preferably glass. The receptacle may be of any size suitable for holding the additive to be dispensed. Preferred receptacles for the above-described standard blood collection tubes have a capacity of about 600 uL and are made from glass tubing (0.6 cm OD, 0.5 cm ID and about 0.5 to 2.0 cm in length). These dimensions allow the receptacle to fit into the cavity within the skirt portion of conventional blood collection tube stoppers with an axial orientation for accessibility to the blood draw cannula.

As described above, the receptacle includes a barrel portion and a film covering over the open bottom end and preferably over both open ends. Preferably the covering is made of a material which is water impermeable and which is puncturable without being resealable. Suitable coverings are films about 0.02 to 0.08 mm thick of water impermeable plastics such as polyolefin and polyvinyl chloride. Preferred coverings are of metal foil of about the same thickness, and may be affixed to the barrel portion by any suitable means, such as glue.

Any additive useful in blood analysis, including both procoagulants and anticoagulants, may be stored in the receptacle. In this way, the assembly, by proper selection of additive, may be used across the entire spectrum of commercial blood collection tubes.

As known in the art, blood analysis is often performed on serum, and procoagulants are often used to enhance the rate of clotting. A representative but not exhaustive list of suitable procoagulants which may be stored in the receptacle are particulate clot activators such as silica particles or enzyme clot activators such as elagic acid, fibrinogen and thrombin. On the other hand, if plasma is needed for analysis, an anticoagulant is generally provided to inhibit coagulation while blood cells are removed by centrifugation. Suitable anticoagulants for the present invention may be, for example, chelators such as oxalates, citrate, and EDTA or enzymes such as heparin.

The additives may be supplied in the receptacle in any desired form, such as a solution in a solvent, preferably water or saline, or as a powdered, crystalline or lyophilized solid.

The choice and quantity of additive to be stored in the receptacle depends on the size of the blood sample and analytical procedure to be performed and are well known to those skilled in the blood analysis art. No further details are needed for a full understanding of this aspect of the invention.

Figure 2:
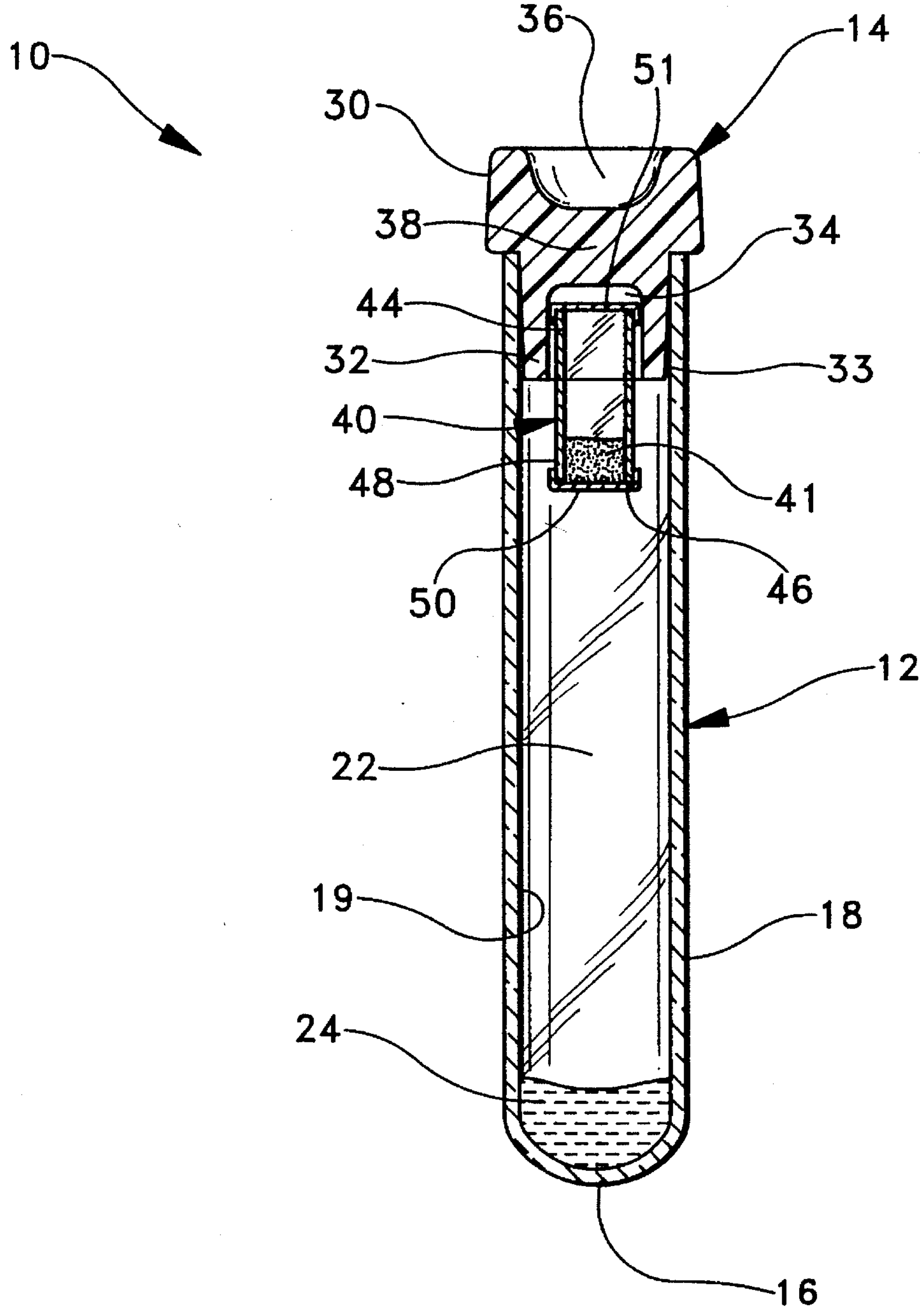
FIG. 2 is a vertical sectional view of the assembly of FIG. 1 taken along the line 2–2_a_ thereof.
Figure 7:
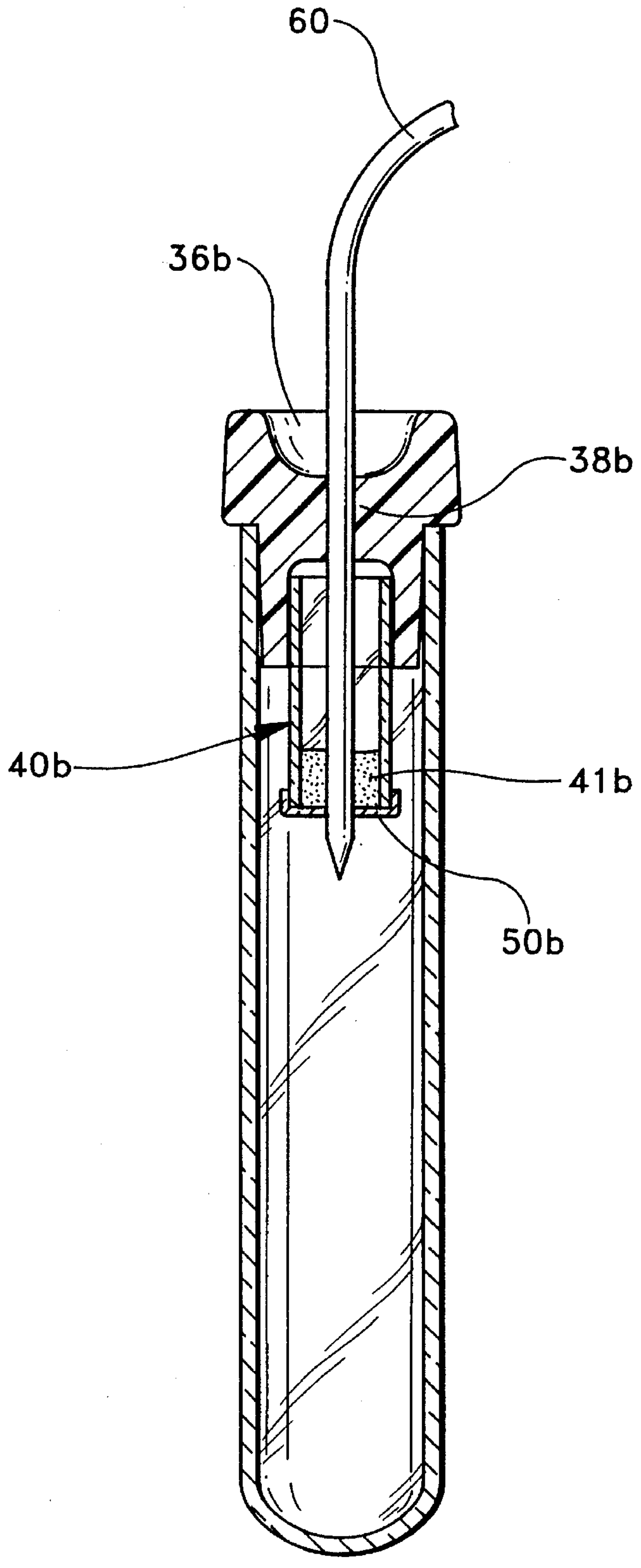
FIG. 7 is a vertical sectional view of the assembly of FIG. 1 showing puncture of the stopper and receptacle by a cannula.
Figure 8:
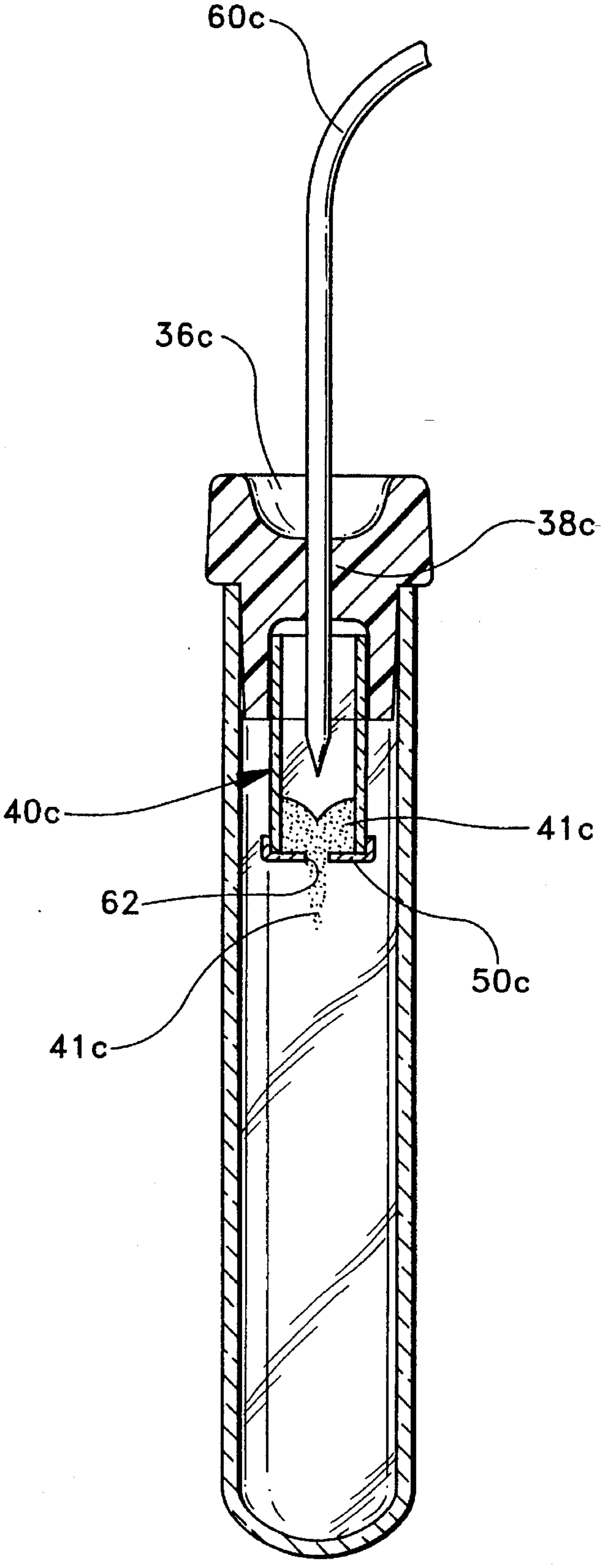
FIG. 8 is a vertical sectional view of the assembly of FIG. 1 after the cannula of FIG. 7 has been partially withdrawn to reside within the receptacle.

As mentioned above, the septum portion of the stopper is pierced by a cannula during blood sampling. FIGS. 7 and 8 illustrate use of the assembly of the invention during blood sampling. In FIG. 7, one end of a cannula 60 is connected to a blood supply such as a patient's vein (not shown in the drawing), and the other end is inserted by puncture through septum **38*b* and through non-resealable covering 50*b*. If the assembly includes the optional covering over the open end (element 51 as shown in FIG. 2, not shown in FIGS. 7 and 8), the cannula will of course also puncture this covering. As soon as puncture of covering 50*b* is achieved, cannula 60 is partially retracted to reside within the receptacle. FIG. 8 shows cannula 60*c* within receptacle 40*c*. After puncture, and because the covering is non-resealable, the covering has a hole 62 therein, through which additive 41*c*** is conveyed by the blood sample.

Puncture and partial retraction of the cannula may easily be performed manually or alternatively may be performed with a spring loaded needle holder which automatically determines the length of cannula insertion for puncture and the length of cannula retraction into the receptacle.

It has been found that, when covering 50 of receptacle 40 is pierced by the cannula, blood draw is initiated by the reduced pressure in the evacuated tube. Blood flow continues upon retraction of the cannula so that the blood is delivered from the cannula directly into the interior volume of the receptacle where it contacts the additive. A vigorous and unexpected vortex mixing of additive and blood in the receptacle is established. If the additive is soluble, such as citrate, it dissolves in the blood; if it is insoluble, such as silica particles, it becomes suspended in the blood. The blood-additive mixture is drawn through the hole by the large pressure differential between the tube and the receptacle and flows to the bottom of the tube.

In the preferred assembly of the invention, the tube is plastic, preferably PET, and the receptacle is a glass tube having foil coverings over both open ends. Thus, the preferred tube has the advantages of plastic, but the disadvantage of plastic, water permeability, is overcome because any water soluble additive is stored in the water impermeable glass receptacle, and no deterioration or change in concentration of the additive takes place.

EXAMPLE I

This example visually demonstrates dispensing an additive from a mixing chamber into an evacuated tube upon vacuum draw of a liquid from a syringe.

A mixing chamber was fabricated from a 2.5 cm length of 0.6 cm OD glass tubing with aluminum foil epoxied to one opening. After the epoxy dried, approximately 200 uL of a methylene blue dye solution was pipetted into the chamber. The chamber was sealed by gluing foil to the remaining opening. The mixing chamber was press-fit into the skirt of a VACUTAINER™ brand blood collection tube stopper (Becton, Dickinson and Company). The stopper was assembled into a standard glass blood collection tube after evacuating atmospheric gases.

A 10 ml syringe was filled with water and fitted with a 22 gauge needle. The needle was pushed into the stopper of the prepared tube so that the needle punctured the stopper and, momentarily, both top and bottom foil sealing elements of the mixing chamber. Immediately after puncture, a small volume of water began to enter the tube and the needle was retracted into the body of the mixing chamber. At this time, a rapid vortex mixing effect was noted in the mixing chamber and the dye was rapidly dispensed through the hole made by the needle into the evacuated tube with thorough rinsing as water continued to be drawn into the tube until the vacuum was dissipated.

EXAMPLE II

This experiment demonstrates dispensing of a procoagulant from a mixing chamber to achieve rapid coagulation of blood.

A. Two mixing chambers were fabricated from 2 cm lengths of 0.6 cm OD polystyrene tubing (Becton Dickinson) with 3 mil (0.0762 mm) polystyrene film (Atlantic Plastics) epoxied to one opening. After the epoxy dried, approximately 640 uL of a 1 mg/ml suspension of micronized silica particles (Min-U-Cil™, Pennsylvania Sand and Glass, 5.6 $m^2$/gm) in trichlorotrifluoroethane were pipetted into each of the chambers. Solvent was allowed to evaporate so that each chamber contained $36\times10^4$ $m^2$ available surface area. Mixing chambers containing the dried silica clot activators were press-fit into stoppers of VACUTAINER™ brand blood collection tubes without top-sealing films and assembled into PET tubes after evacuating atmospheric gases.

Blood was drawn from a pig using a 10 ml syringe and immediately drawn from the syringe into the above-prepared tubes in the manner described in Example I. One tube was inverted 5 times to insure dispersal of the silica particles and the other tube was placed upright into a tube rack with no additional mixing other that the vortexing action of the mixing chamber. Coagulation and clean separation of clot from serum was obtained in both cases within 6 minutes. This demonstrates that the silica particles were dispensed from the chamber with mixing with the blood.

B. (control) A PET tube was prepared with a mixing chamber as described in A except that no silica activator was added to the chamber. Blood drawn into this tube through the mixing chamber did not clot after 10 minutes. Blood drawn into a standard glass blood collection tube without a mixing chamber did not clot until 12 minutes. These observations verify that coagulation noted in the tubes of A was due to the dispensed activator.

C. (control) PET tubes without mixing chambers were prepared with silica activator in the bottom of the tube by the volumetric addition from solvent dispersion described in A. Evaporation of solvent resulted in an easily-dispersed residue of silica activator in the tube. Tubes were evacuated and stoppered as above with care not to loosen the dried activator powder. Pig blood drawn into these tubes coagulated within 6 minutes both with and without inversions, demonstrating clot activation equivalent to that observed using the mixing chamber (IIA).

EXAMPLE III

This example demonstrates dispensing of anticoagulants from a mixing chamber.

Blood collection tubes were prepared as described in Example I with mixing chambers containing either 400 ul of 1 mg/ml heparin (168.4 units/mg, Sigma) or 0.104 M sodium citrate. Porcine blood drawn into these tubes through the mixing chambers did not coagulate, demonstrating that these anticoagulants were adequately dispensed from the mixing chamber and mixed with blood.

What is claimed is:

1. A blood collection assembly comprising;

a) a tube having a bottom wall and a side wall defining an open end;

b) a puncturable stopper sealably immobilized in said open end, said bottom wall, side wall and stopper enclosing an evacuated interior volume in said tube, said stopper comprising an annular upper portion and a lower skirt portion, said skirt portion defining a well;

c) a receptacle immobilized in said well, said receptacle comprising a side wall and a puncturable non-resealable bottom wall; and d) an additive in said receptacle for use in analysis of blood.

2. The assembly of claim 1 wherein said receptacle is immobilized in said well by an interference fit between said skirt portion and the receptacle side wall.

3. The assembly of claim 1 wherein an upper edge of said receptacle side wall is in sealing contact with the annular upper portion of said stopper whereby said receptacle side wall and bottom wall and the stopper annular upper portion define an enclosed mixing chamber in the interior of said receptacle.

4. The assembly of claim 2 wherein said receptacle further comprises a puncturable top wall, said receptacle side wall, top wall and bottom wall defining an enclosed mixing chamber.

5. A method for preparing a blood sample for analysis using the assembly of claim 1 comprising;

a) puncturing said stopper and the bottom wall of said receptacle with a first end of a double ended cannula, a second end of said cannula being in fluid communication with a reservoir containing a blood sample to be analyzed, said puncturing defining a hole in said non-resealable bottom wall;

b) retracting said cannula through said hole but not through said stopper whereby blood is drawn by a pressure differential from said reservoir into the receptacle; and c) allowing the blood drawn into the receptacle to contact the additive in the receptacle so that said blood and said additive flow through said hole into said tube.

* * * * *